US009542526B2

(12) United States Patent
Cao

(10) Patent No.: US 9,542,526 B2
(45) Date of Patent: Jan. 10, 2017

(54) METHOD AND SYSTEM FOR TEMPERATURE CORRECTION IN THERMAL MELT ANALYSIS

(75) Inventor: Weidong Cao, Rockville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 12/401,171

(22) Filed: Mar. 10, 2009

(65) Prior Publication Data

US 2010/0233687 A1 Sep. 16, 2010

(51) Int. Cl.
*C12Q 1/68* (2006.01)
*G06F 19/12* (2011.01)
*G06F 19/16* (2011.01)

(52) U.S. Cl.
CPC .............. *G06F 19/12* (2013.01); *G06F 19/16* (2013.01)

(58) Field of Classification Search
None
See application file for complete search history.

(56) References Cited

U.S. PATENT DOCUMENTS

| | | | |
|---|---|---|---|
| 6,174,670 B1 | 1/2001 | Wittwer et al. | |
| 6,232,079 B1 | 5/2001 | Wittwer et al. | |
| 6,889,143 B2 | 5/2005 | Behlke et al. | |
| 6,960,437 B2 | 11/2005 | Enzelberger et al. | |
| 7,198,897 B2 | 4/2007 | Wangh et al. | |
| 2002/0197630 A1 | 12/2002 | Knapp et al. | |
| 2004/0091862 A1 | 5/2004 | Brandenburg et al. | |
| 2005/0042639 A1 | 2/2005 | Knapp et al. | |
| 2005/0053950 A1 | 3/2005 | Zudaire Ubani et al. | |
| 2005/0233335 A1 | 10/2005 | Wittwer et al. | |
| 2006/0019253 A1 | 1/2006 | Wittwer et al. | |
| 2007/0020672 A1 | 1/2007 | Wittwer et al. | |
| 2007/0026421 A1 | 2/2007 | Sundberg et al. | |
| 2007/0231799 A1 | 10/2007 | Knight et al. | |

FOREIGN PATENT DOCUMENTS

WO 2005/075683 A1 8/2005

OTHER PUBLICATIONS

Marky et al. Calculating thermodynamic data for transitions of any molecularity from equilibrium melting curves. Biopolymers, vol. 26, 1987, pp. 1601-1620.*
Owczarzy et al. Predicting sequence-dependent melting stability of short duplex DNA oligomers. Biopolymers, vol. 44, 1997, pp. 217-239.*
Equilibrium constant. Academic Press Dictionary of Science and Technology, 1992, one pages. Retrieved online on Mar. 24, 2011 from <<http://www.credoreference.com/entry/apdst/equilibrium_constant>>.*
Freezing point, depression of; 2 pages. The Hutchinson Unabridged Encyclopedia with Atlas and Weather Guide, 2010. Retrieved online on Nov. 25, 2011 from <<http://www.credoreference.com/entry/heliconhe/freezing_point_depression_of>>.*
Guanosine. Sigma-Aldrich Catalog, 2 pages, 2012. Obtained online on Aug. 13, 2012 from <<http://www.sigmaaldrich.com>>.*
Xu et al. International Journal of Systematic and Evolutionary Microbiology, 2000, vol. 50, pp. 1463-1469.*
Gudnason et al. Nucleic Acids Research, 2007, vol. 35, p. e127, eight pages.*
Melting Temperature, Genosys Biotechnologies, Inc., 1998. Obtained online <<http://www.sigmaaldrich.com/img/assets/17240/meltingtemp.pdf>>.*
Meinkoth et al. Hybridization of nucleic ac ids immobilized on solid supports. Analytical Biochemistry, vol. 138, 1994, pp. 267-284.*
Milev et al. Energetics for sequence-specific protein-DNA association: Binding of integrase Tn916 to its target DNA. Biochemistry, 2003, vol. 42, pp. 3481-3491.*
Castellan GW. Physical Chemistry, Third Edition, 1983. Section 13.6, pp. 282-285.*
Ahsen et al., "Limitations of Genotyping Based on Amplicon Melting Temperature," Clinical Chemistry, 47 (7):1331-1332 (2001).
Kopp et al., "Chemical Amplification: Continuous-Flow PCR on a Chip," Science, vol. 280, pp. 1046-1048 (1998).
Lagally et al., "Single-Molecule DNA Amplification and Analysis in an Integrated Microfluidic Device," Analytical Chemistry, vol. 73, No. 3, pp. 565-570 (2001).
Novere, "Melting, computing the melting temperature of nucleic acid duplex," Bioinformatics, 17(12):1226-1227 (2001).
Park et al., "Cylindrical compact thermal-cycling device for continuous-flow polymerase chain reaction," Analytical Chemistry, vol. 75, pp. 6029-6033 (2003).
Rychlik et al., "Optimization of the annealing temperature for DNA amplification in vitro," Nucleic Acids Research, 18 (21):6409-6412 (1990).
Lipsky et al., "DNA Melting Analysis for Detection of Single Nucleotide Polymorphisms," Clin. Chem., vol. 47, No. 4, pp. 635-344 (2001).
Leber et al., "A Fractional Programming Approach to Efficient DNA Melting Temperature Calculation," Bioinformatics, vol. 21, No. 10, pp. 2375-2382 (2005).
Petruska et al., "Enthalpy-Entropy Compensation in DNA Melting Thermodynamics," JBC, vol. 270, No. 2, pp. 746-750 (1995).
Santalucia et al., "Improved Nearest-Neighbor Parameters for Predicting DNA Duplex Stability," Biochemistry, vol. 35, pp. 3555-3562 (1996).

* cited by examiner

Primary Examiner — Russell S Negin
(74) Attorney, Agent, or Firm — Rothwell, Figg, Ernst & Manbeck, P.C.

(57) ABSTRACT

The present invention relates to methods and systems for temperature correction in thermal melt analysis. More specifically, embodiments of the invention relate to the correction of the melting temperature ($T_m$) observed for a sample nucleic acid due to the effect of the nucleic acid concentration.

12 Claims, 3 Drawing Sheets

METHOD AND SYSTEM FOR TEMPERATURE CORRECTION IN THERMAL MELT ANALYSIS

BACKGROUND

Field of the Invention

The present invention relates to methods and systems for temperature correction in thermal melt analysis. More specifically, embodiments of the invention relate to the correction of the melting temperature observed for a sample nucleic acid due to the effect of the nucleic acid concentration.

Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR, see *Real-Time PCR: An Essential Guide*, K. Edwards et al., eds., Horizon Bioscience, Norwich, U.K. (2004).

More recently, a number of high throughput approaches to performing PCR and other amplification reactions have been developed, for example, involving amplification reactions in microfluidic devices, as well as methods for detecting and analyzing amplified nucleic acids in or on the devices. Thermal cycling of the sample for amplification in microfluidic devices is usually accomplished in one of two methods. In the first method, the sample solution is loaded into the device and the temperature is cycled in time, much like a conventional PCR instrument. In the second method, the sample solution is pumped continuously through spatially varying temperature zones. See, e.g., Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA) with increasing temperature. The process of causing DNA to transition from dsDNA to ssDNA is sometimes referred to as a "high-resolution temperature (thermal) melt (HRTm)" process, or simply a "high-resolution melt" process.

Melt curve analysis is an important technique for analyzing nucleic acids. In accordance with some methods, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is raised, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence. See, e.g., Ririe et al. (*Anal Biochem* 245:154-160, 1997), Wittwer et al. (*Clin Chem* 49:853-860, 2003), Liew et al. (*Clin Chem* 50:1156-1164 (2004), Herrmann et al. (*Clin Chem* 52:494-503, 2006), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253), Sundberg et al. (U.S. Patent Application Publication No. 2007/0026421) and Knight et al. (U.S. Patent Application Publication No. 2007/0231799).

Some nucleic acid assays require identification of a single nucleotide change where the difference in melting temperature ($T_m$) between the wild type nucleic acid and the mutant nucleic acid is less than, for example, 0.25° C. This level of temperature resolution is difficult, if not impossible, in standard 96 and 384 well plates. Decreasing the area of thermal analysis may improve the spatial temperature gradient, but there is still significant noise generated from the heating device used to linearly ramp the samples during a thermal melt. In addition, the concentration of the nucleic acid is known to affect the $T_m$ that is determined for sample nucleic acid. Melting temperatures are often determined following amplification of a nucleic acid sample. In order to avoid nucleic acid concentration effects, the amplification reactions are conventionally performed to the plateau phase. However, it has been observed that amplification reactions performed in microfluidic devices do not reach the plateau phase, thus creating differences in nucleic acid concentrations between the microchannels of the device. Accordingly, what are desired are methods and systems for high resolution melt analysis that are capable of more accurately providing a $T_m$ for the sample nucleic acid. Also desired are methods and systems for high resolution melt analysis that more accurately identify $T_m$ that facilitate detection of sequence information for DNA that contain one or more mutations.

SUMMARY OF THE INVENTION

The present invention relates to methods and systems for temperature correction in thermal melt analysis. More specifically, embodiments of the invention relate to the correction of the melting temperature ($T_m$) observed for a sample nucleic acid due to the effect of the nucleic acid concentration.

In one aspect, the present invention provides a method for correcting a measured melting temperature of a nucleic acid in a sample. According to this aspect, the method comprises the steps of: (a) determining a ratio of the concentration of the nucleic acid in a reference sample to the concentration of the nucleic acid in the sample; (b) measuring the melting temperature of the nucleic acid in the sample and the melting temperature of the nucleic acid in the reference sample; (c) determining a temperature compensation value from said ratio; and (d) correcting the measured melting temperature of the nucleic acid in the sample with the temperature compensation value to provide a corrected melting temperature of the nucleic acid in the sample.

In one embodiment, the method includes in step (c) the determination of the change of enthalpy ($\Delta H^0$) of the nucleic acid in the reference sample. In some embodiments, $\Delta H^0$ of the nucleic acid in the reference sample is determined by the equation $T_{m1\ (measured)} \times N_{base\ pair} \times \Delta S_{bp}$, wherein $T_{m1\ (measured)}$ is the measured melting temperature of the nucleic acid in the reference sample, $N_{base\ pair}$ is the number of base pairs in the nucleic acid and $\Delta S_{bp}$ is the change in entropy per base pair. In further embodiments, the temperature compensation value is $\Delta T_m$, wherein $\Delta T_m$ is $T_{m2} - T_{m1}$, wherein $T_{m1}$ is the measured melting temperature of the nucleic acid in the reference sample and $T_{m2}$ is the melting temperature resulting from a difference in concentration of the nucleic acid.

In some embodiments, $T_{m2}$ is calculated by the equation $$\frac{1}{T_{m2}} = \frac{1}{T_{m1}} - \frac{R\ln\left(\frac{C1}{C2}\right)}{\Delta H^0}$$

wherein R is the gas constant and C1/C2 is the ratio of the concentration of the nucleic acid in the reference sample to the concentration of the nucleic acid in the sample.

In other embodiments, the measured melting temperature of the nucleic acid in the sample is corrected by subtracting $\Delta T_m$ from the measured melting temperature of nucleic acid in the sample.

In further embodiments, the ratio of the concentrations of the nucleic acid in the reference sample and in the sample is determined after amplification of the nucleic acid in the sample and amplification of the nucleic acid in the reference sample. In some embodiments, the ratio is determined by fluorescence. In other embodiments, the amplifications are performed in microchannels. In further embodiments, the amplifications are performed in continuous flow in the microchannels. In some embodiments, the melting temperatures are measured in a continuous melt.

In another aspect, the present invention provides a system for correcting a melting temperature of a nucleic acid in a sample. In accordance with this aspect, the system comprises a temperature compensation module capable of determining a temperature compensation value from a ratio of the concentration of the nucleic acid in a reference sample to the concentration of the nucleic acid in the sample and a measured melting temperature of the nucleic acid in the reference sample. The system further comprises a correction module capable of correcting the measured melting temperature of the nucleic acid in the sample by subtracting the temperature compensation value from the measured melting temperature of the nucleic acid in the sample to provide a corrected melting temperature of the nucleic acid in the sample.

In some embodiments, the temperature compensation module determines the change of enthalpy ($\Delta H^0$) of the nucleic acid in the reference sample. In other embodiments, $\Delta H^0$ of the nucleic acid in the reference sample is determined by the equation $T_{m1\ (measured)} \times N_{base\ pair} \times \Delta S_{bp}$, wherein $T_{m1\ (measured)}$ is the measured melting temperature of the nucleic acid in the reference sample, $N_{base\ pair}$ is the number of base pairs in the nucleic acid and $\Delta S_{bp}$ is the change in entropy per base pair. In further embodiments, the temperature compensation value is $\Delta T_m$, wherein $\Delta T_m$ is $T_{m2} - T_{m1}$, wherein $T_{m1}$ is the measured melting temperature of the nucleic acid in the reference sample and $T_{m2}$ is the melting temperature resulting from a difference in concentration of the nucleic acid.

In some embodiments, $T_{m2}$ is calculated by the equation $$\frac{1}{T_{m2}} = \frac{1}{T_{m1}} - \frac{R\ln\left(\frac{C1}{C2}\right)}{\Delta H^0}$$

wherein R is the gas constant and C1/C2 is the ratio of the concentration of the nucleic acid in the reference sample to the concentration of the nucleic acid in the sample.

In some embodiments, the temperature compensation module includes a computer containing instructions for determining the temperature compensation value. In other embodiments, the system further comprises a measuring unit capable of measuring the melting temperature of the nucleic acid of the sample and the nucleic acid of the reference sample. In further embodiments, the measuring unit further measures the ratio of the concentration of the nucleic acid in the reference sample to the nucleic acid in the sample.

BRIEF DESCRIPTION OF THE FIGURES

The accompanying drawings, which are incorporated herein and form part of the specification, illustrate various embodiments of the present invention.

DETAILED DESCRIPTION OF PREFERRED EMBODIMENTS

Figure 1:
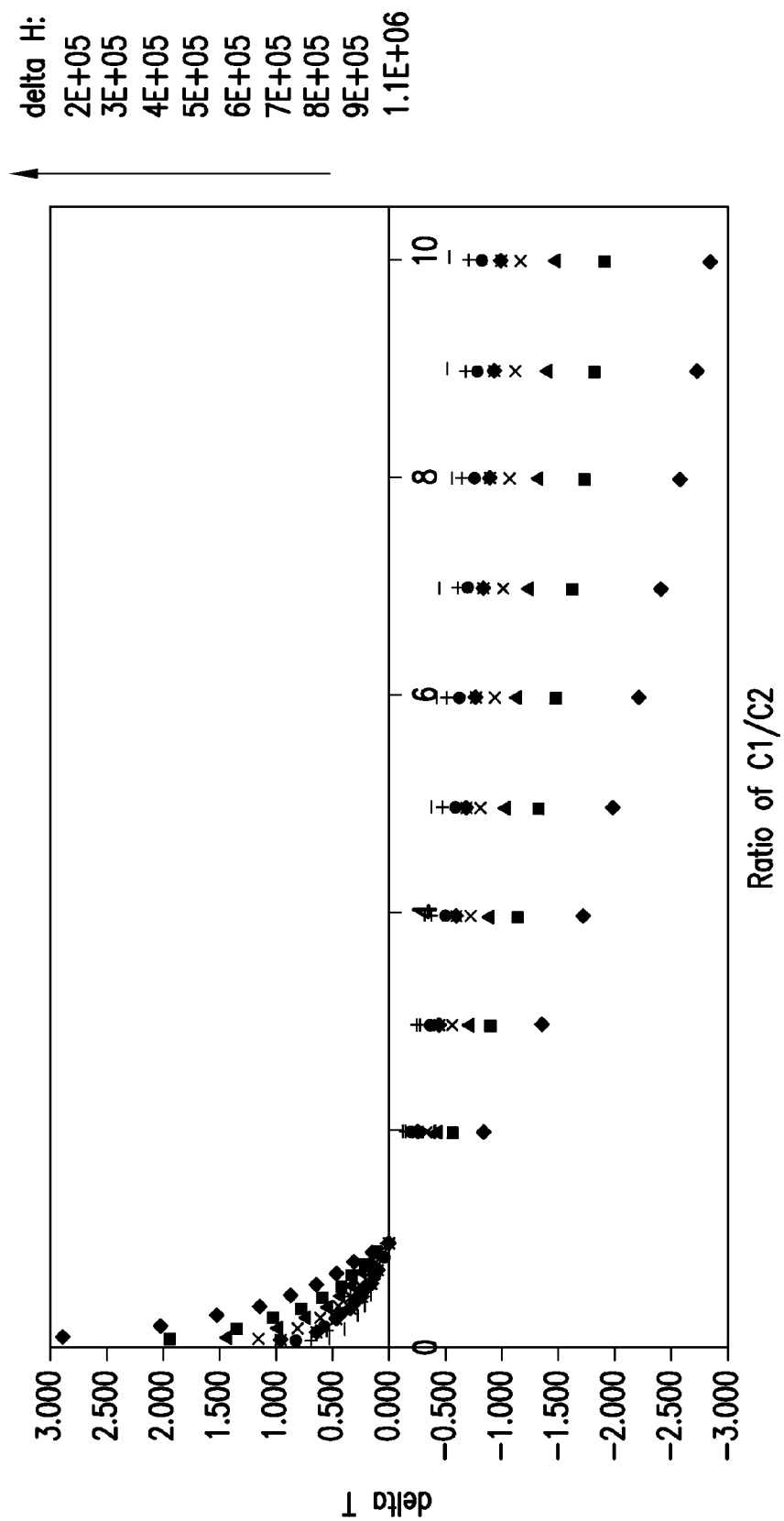
FIG. 1 illustrates the effect of DNA concentration on the melting temperature.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger, *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

Thermal melt curves of fluorescence have been used to determine the melting temperature of a DNA strand when denatured from the duplex state to the two separate single strands via a ramp increase in temperature. Typically, the melting temperature or $T_m$ is defined to be the temperature at which 50% of the paired DNA strands have denatured into single strands. Intercalating dyes that fluoresce when bound to double stranded DNA and lose their fluorescence when denatured are often used in measuring $T_m$. Typically, the negative derivative of fluorescence with respect to temperature ($-dF/dT$) has been used in the determination of $T_m$. In typical systems, the temperature at the peak $-dF/dT$ is used as an estimate of the melting temperature $T_m$.

Melting curve analysis is typically carried out either in a stopped flow format or in a continuous flow format. In one example of a stopped flow format, flow is stopped within a microchannel of a microfluidic device while the temperature in that channel is ramped through a range of temperatures required to generate the desired melt curve. In an alternative stopped flow format, melting curve analysis is done in a chamber to which the nucleic acid sample has been added. In one example of a continuous flow format, a melting curve analysis is performed by applying a temperature gradient along the length (direction of flow) of a microchannel of a microfluidic device. If the melting curve analysis requires that the molecules being analyzed be subjected to a range of temperatures extending from a first temperature to a second temperature, the temperature at one end of the microchannel is controlled to the first temperature, and the temperature at the other end of the length is controlled to the second temperature, thus creating a continuous temperature gradient spanning the temperature range between the first and second selected temperatures. An example of an instrument for performing a melting curve analysis is disclosed in U.S. Patent Application Publication No. 2007/0231799, incorporated herein by reference in its entirety.

The thermal melt data that is analyzed in accordance with aspects of the present invention is obtained by techniques well known in the art. See, e.g., Knight et al. (U.S. Patent Application Publication No. 2007/0231799); Knapp et al. (U.S. Patent Application Publication No. 2002/0197630); Wittwer et al. (U.S. Patent Application Publication No. 2007/0020672); and Wittwer et al. (U.S. Pat. No. 6,174,670). Although the present invention is applicable to the analysis of thermal melt data obtained in any environment, it is particularly useful for thermal melt data obtained in the microfluidic environment because of the need for greater sensitivity in this environment.

In accordance with certain aspects of the invention, thermal melt data is generated by elevating the temperature of a molecule or molecules, e.g., of one or more nucleic acids, for a selected period of time and measuring a detectable property emanating from the molecule or molecules, wherein the detectable property indicates an extent of denaturation of the nucleic acid. This period of time can range, for example, from about 0.01 second through to about 1.0 minute or more, from about 0.01 second to about 10 seconds or more, or from about 0.1 second to about 1.0 second or more, including all time periods in between. In one embodiment, heating comprises elevating the temperature of the molecule or molecules by continuously increasing the temperature of the molecule or molecules. For example, the temperature of the molecule(s) can be continuously increased at a rate in the range of about 0.1° C./second to about 1° C./second. Alternatively, the temperature of the molecule(s) can be continuously increase at a slower rate, such as a rate in the range of about 0.01° C./second to about 0.1° C./second, or at a faster rate, such as a rate in the range of about 1° C./second to about 10° C./second. The heating can occur through application of an internal or an external heat source, as is known in the art.

The actual detection of a change(s) in a physical property of the molecules can be detected in numerous methods depending on the specific molecules and reactions involved. For example, the denaturation of the molecules can be tracked by following fluorescence or emitted light from molecules in the assay. The degree of, or change in, fluorescence is correlational or proportional to the degree of change in conformation of the molecules being assayed. Thus, in some methods, the detection of a property of the molecule(s) comprises detecting a level of fluorescence or emitted light from the molecules(s) that varies as a function of relative amounts of binding. In one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule.

In aspects of the present invention, the thermal melt data can be used to generate a thermal property curve. In some methods, the generation of a thermal property curve includes providing one molecule comprising a fluorescence indicator dye or fluorescence indicator molecule, and at least a second molecule comprising, one or more of an enzyme, a ligand, a peptide nucleic acid, a cofactor, a receptor, a substrate, a protein, a polypeptide, a nucleic acid (either double-stranded or single-stranded), an antibody, an antigen, or an enzyme complex. Fluorescence of the first molecule in the presence of the second molecule as a function of temperature is measured and the resulting data is used to generate a thermal property curve. In other methods, the generation of a thermal property curve comprises measuring a change in the fluorescence of one molecule that is correlative or proportional to a change in a physical property of another molecule(s) due to a change in temperature. In still other methods, the generation of a thermal property curve comprises measuring the change in the total free energy of the system as a function of temperature without the presence of a second molecule. Typically, the methods also include generating a thermal property curve of a control or known sample in a similar manner.

Several techniques exist for the measurement of the denaturation of the molecules of interest, and any of these can be used in generating the data to be analyzed in accordance with aspects of the present invention. Such techniques include fluorescence, fluorescence polarization, fluorescence resonance energy transfer, circular dichroism and UV absorbance. Briefly, the fluorescence techniques involves the use of spectroscopy to measure changes in fluorescence or light to track the denaturation/unfolding of the target molecule as the target molecule is subjected to changes in temperature. Spectrometry, e.g. via fluorescence, is a useful method of detecting thermally induced denaturation/unfolding of molecules. Many different methods involving fluorescence are available for detecting denaturation of molecules (e.g. intrinsic fluorescence, numerous fluorescence indicator dyes or molecules, fluorescence polarization, fluorescence resonance energy transfer, etc.) and are optional embodiments of the present invention. These methods can take advantage of either internal fluorescent properties of target molecules or external fluorescence, i.e. the fluorescence of additional indicator molecules involved in the analysis.

A method of measuring the degree of denaturation/unfolding of the target molecule is through monitoring of the fluorescence of dyes or molecules added to the microfluidic device along with the target molecule and any test molecules of interest. A fluorescence dye or molecule refers to any fluorescent molecule or compound (e.g., a fluorophore) which can bind to a target molecule either once the target molecule is unfolded or denatured or before the target molecule undergoes conformational change by, for example, denaturing and which emits fluorescent energy or light after it is excited by, for example, light of a specified wavelength.

One dye type used in the microfluidic devices is one that intercalates within strands of nucleic acids. An example of such a dye is ethidium bromide. An exemplary use of ethidium bromide for binding assays includes, for example, monitoring for a decrease in fluorescence emission from ethidium bromide due to binding of test molecules to nucleic acid target molecules (ethidium bromide displacement assay). See, e.g., Lee, M. et al. (*J Med Chem* 36(7):863-870 (1993)). The use of nucleic acid intercalating agents in measurement of denaturation is known to those in the art. See, e.g., Haugland (*Handbook of Fluorescent Probes and Research Chemicals*, Molecular Probes, Inc., Eugene, Oreg. (1996)).

Dyes that bind to nucleic acids by mechanisms other than intercalation can also be employed in embodiments of the invention. For example, dyes that bind the minor groove of double stranded DNA can be used to monitor the molecular unfolding/denaturation of the target molecule due to temperature. Examples of suitable minor groove binding dyes are the SYBR Green family of dyes sold by Molecular Probes Inc. (Eugene, Oreg., USA). See, e.g., Haugland (*Handbook of Fluorescent Probes and Research Chemicals*, Molecular Probes, Inc., Eugene, Oreg., USA (1996)). SYBR Green dyes will bind to any double stranded DNA molecule. When a SYBR Green dye binds to double stranded DNA, the intensity of the fluorescent emissions increases. As more double stranded DNA are denatured due to increasing temperature, the SYBR Green dye signal will decrease. Another suitable dye is LCGreen Plus sold by Idaho Technology, Inc. (Salt Lake City, Utah, USA).

Fluorescence polarization (FP) provides a useful method to detect hybridization formation between molecules of interest. This method is especially applicable to hybridization detection between nucleic acids, for example, to monitor single nucleotide polymorphisms (SNPs). Generally, FP operates by monitoring, the speed of rotation of fluorescent labels, such as fluorescent dyes or molecular beacons, e.g. before, during, and/or after binding events between molecules that comprise the test and target molecules. In short, binding of a test molecule to the target molecule ordinarily results in a decrease in the speed of rotation of a bound label on one of the molecules, resulting in a change in FP.

Fluorescence resonance energy transfer (FRET) can be used to track the conformational changes of the target molecule (and interactions with test molecules which can bind with the target molecule) as a function of temperature. FRET relies on a distance-dependent transfer of energy from a donor fluorophore to an acceptor fluorophore. If an acceptor fluorophore is in close proximity to an excited donor fluorophore, then the emission of the donor fluorophore can be transferred to the acceptor fluorophore. This causes a concomitant reduction in the emission intensity of the donor fluorophore and an increase in the emission intensity of the acceptor fluorophore. Since the efficiency of the excitation transfer depends, inter alia, on the distance between the two fluorophores, the technique can be used to measure extremely small distances such as would occur when detecting changes in conformation. This technique is particularly suited for measurement of binding reactions, protein-protein interactions, e.g., such as a protein of interest binding to an antibody and other biological events altering the proximity of two labeled molecules. Many appropriate interactive labels are known. For example, fluorescent labels, dyes, enzymatic labels, and antibody labels are all appropriate.

Circular dichroism (CD) can be used to follow the conformational changes of the target molecules/text molecules as a function of temperature and can be used to construct molecular melt curves. CD is a type of light absorption spectroscopy which measures the difference in absorbance by a molecule between right-circularly polarized light and left-circularly polarized light. CD is quite sensitive to the structure of polypeptides and proteins.

UV absorbance can also be used to detect and/or track denaturation of nucleic acid molecules, and/or to quantify the total amount of nucleic acid. UV can be employed to measure the extent of denaturation because the UV absorbance value of single stranded nucleic acid molecules is greater than the absorbance value of double stranded nucleic acid molecules.

Once the denaturation data has been obtained and melt curves generated, if desired, the data and/or melt curves are then analyzed to determine the measured melting temperature of the nucleic acid in the sample. It is expected, based on known thermodynamic relationships, that changes in nucleic acid concentration will effect the detection of $T_m$. If the nucleic acid concentrations are different among samples and between a reference sample, such differences will cause errors in the $T_m$s of the samples. Differences in nucleic acid concentrations among samples and between a reference sample can occur in amplification reactions, especially as a result of different starting nucleic acid concentrations in such samples. Because the nucleic acid concentration is unknown in most amplification reactions, it is difficult to obtain an absolute measured $T_m$. Thus, it is desired to correct the measured $T_m$s to take into account differences in nucleic acid concentrations. In accordance with the present invention, methods and systems are provided to correct the measured melting temperature of the nucleic acid in the sample for such concentration effects.

In accordance with certain aspects, the present invention provides a method for correcting a measured melting temperature of a nucleic acid in a sample. According to this aspect, the method comprises the steps of: (a) determining a ratio of the concentration of the nucleic acid in a reference sample to the concentration of the nucleic acid in the sample; (b) measuring the melting temperature of the nucleic acid in the sample and the melting temperature of the nucleic acid in the reference sample; (c) determining a temperature compensation value from said ratio; and (d) correcting the measured melting temperature of the nucleic acid in the sample with the temperature compensation value to provide a corrected melting temperature of the nucleic acid in the sample. Standard thermodynamic relationships are utilized in accordance with the present invention to obtain corrected melting temperatures.

According to standard thermodynamic relationships, the melting temperature of a nucleic acid can be defined by the following equation.

$$T_m = \frac{\Delta H^0}{\Delta S^0 - R\ln(4/C^0)},$$ (equation 1)

wherein $\Delta H^0$ is the change in enthalpy, $\Delta S^0$ is the change in entropy and $C^0$ is the concentration of the double-stranded nucleic acid. Thus, the melting temperature for a first nucleic acid sample can be expressed as $$T_{m1} = \frac{\Delta H^0}{\Delta S^0 - R\ln(4/C^1)},$$ (equation 2)

wherein C1 is the concentration of the first nucleic acid, and the melting temperature for a second nucleic acid sample can be expressed as $$T_{m2} = \frac{\Delta H^0}{\Delta S^0 - R\ln(4/C^2)},$$ (equation 3)

wherein C2 is the concentration of the second nucleic acid.

The effect of the concentration on melting temperature can be expressed by the following equation:

$$\frac{1}{T_{m1}} - \frac{1}{T_{m2}} = \frac{R\ln\left(\frac{C1}{C2}\right)}{\Delta H^0}.$$ (equation 4)

Equation 4 can be alternatively expressed as follows:

$$\frac{1}{T_{m2}} = \frac{1}{T_{m1}} - \frac{R\ln\left(\frac{C1}{C2}\right)}{\Delta H^0}.$$ (equation 5)

In accordance with certain embodiments of the present invention, the shift in the melting temperature resulting from a difference in nucleic acid concentration can be calculated by measuring the ratio of the concentrations of the nucleic acid in the samples. FIG. 1 illustrates an example of the effect of DNA concentration on melting temperature. As shown in the illustrative example of FIG. 1, the shift in melting temperature can be as high as 0.43° C. when the change in enthalpy is 35 Kcal/mol and the concentration ratio is 0.6. In accordance with the present invention, the ratio of the nucleic acid in the samples can be performed by any method that can provide a relative value on the amount of nucleic acid in each sample. For example, in accordance with certain aspects of the present invention, the ratio of nucleic acids concentrations can be determined by measuring the fluorescence of the nucleic acid in the samples following amplification reactions, such as polymerase chain reaction amplifications.

As evident from the above equations, the change in enthalpy is the only factor affecting the shift in melting temperature caused by differences in nucleic acid concentrations. Once the change in enthalpy is known, a temperature compensation value can be determined from the above equations. The measured melting temperature can be corrected using this temperature compensation value to obtain a more precise melting temperature for the nucleic acid in the sample.

In accordance with certain aspects of the present method, step (c) includes the determination of the change of enthalpy ($\Delta H^0$) of the nucleic acid in the reference sample. In some embodiments, $\Delta H^0$ of the nucleic acid in the reference sample is determined by the equation $$T_{m1\ (measured)} \times N_{base\ pair} \times \Delta S_{bp}$$ (equation 6).

In this equation $T_{m1\ (measured)}$ is the measured melting temperature of the nucleic acid in the reference sample, $N_{base\ pair}$ is the number of base pairs in the nucleic acid and $\Delta S_{bp}$ is the change in entropy per base pair. In some embodiments, the $\Delta S_{bp}$ is equal to $-24.85$ cal mol$^{-1}$K$^{-1}$ (Owczarzy et al., *Biopolymers* 44:217-239 (1997)). The number of base pairs in the nucleic acid is the number of base pairs of the target sequence that is being amplified in the amplification reaction, i.e., the number of base pairs of the amplicon.

In further embodiments, the temperature compensation value is expressed as $\Delta T_m$, wherein $$\Delta T_m = T_{m2} - T_{m1}$$ (equation 7).

In this equation, $T_{m1}$ is the measured melting temperature of the nucleic acid in the reference sample and $T_{m2}$ is the melting temperature that results from a difference in concentration of the nucleic acid. As described above, $T_{m2}$ is determined by the following equation:

$$\frac{1}{T_{m2}} = \frac{1}{T_{m1}} - \frac{R\ln\left(\frac{C1}{C2}\right)}{\Delta H^0}.$$ (equation 4)

Once $T_{m2}$ is determined by this equation, the temperature compensation value, i.e., $\Delta T_m$, is determined using equation 7 above. The corrected melting temperature of the nucleic acid in the sample is determined by subtracting the temperature compensation value $\Delta T_m$ from the measured melting temperature of the nucleic acid in the sample as shown in equation 8.

$$T_{m2\ (corrected)} = T_{m2\ (measured)} - \Delta T_m \quad \text{(equation 8)}.$$

In equation 8, $T_{m2}$ is the melting temperature of the nucleic acid in the sample. In one embodiment, the samples, i.e., the samples of genomic nucleic acid and the reference sample containing a known amount of a nucleic acid of the target sequence, include a fluorescent dye for measuring the denaturation of the molecules in the samples. Suitable fluorescent dyes for detecting denaturation of molecules are well known in the art and include those described herein, such as the double-strand specific dyes of the SYBR Green family of dyes and LCGreen Plus. Any suitable fluorescent dye can be used in the methods of the invention. In another embodiment, the relative value of the concentration of nucleic acid in each sample is the fluorescence intensity for that sample. In a further embodiment, the relative value of the concentration of nucleic acid in each sample is intensity of ultraviolet absorbance.

In accordance with certain aspects of the present invention, the melting temperature of a nucleic acid in a sample is determined following amplification of the nucleic acid in the sample. The samples and a reference sample are subjected to amplification under the same conditions. Any amplification reaction can be utilized in the present invention. In one embodiment, the amplification reaction is a polymerase chain reaction amplification. In some embodiments of the present invention, the amplification reactions are performed in a microchannels, such as channels of a microfluidic device. In other embodiments, the amplification reactions are performed in a continuous flow format in the microchannels. In additional embodiments, the melting temperatures of the samples and reference samples are measured in a continuous melt format.

Figure 2:
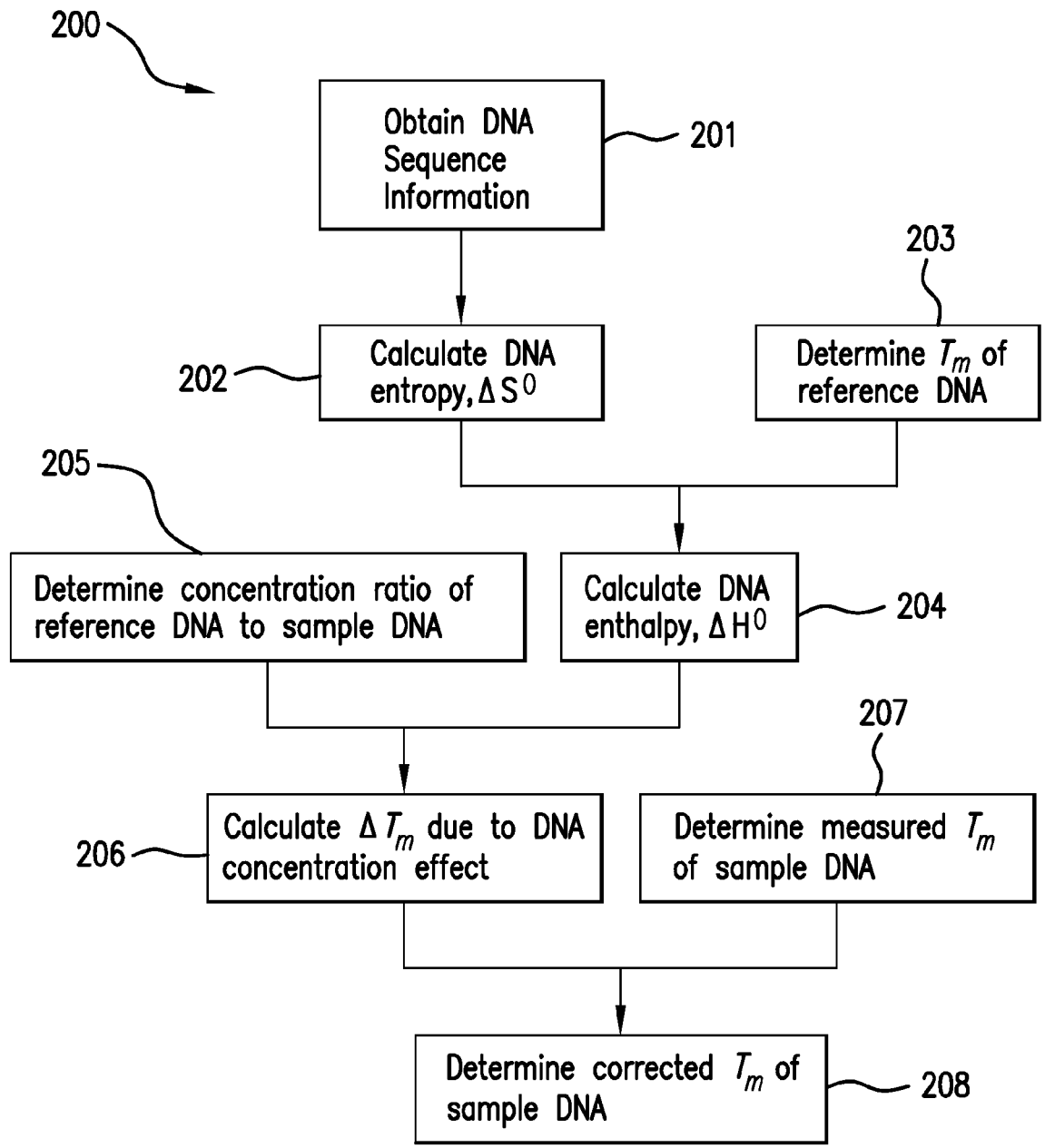
FIG. 2 illustrates a flow chart showing a method in accordance with one aspect of the present invention.

FIG. 2 illustrates a flow chart for a method 200 for correcting the melting temperature of a nucleic acid in a sample in accordance with an embodiment of the present invention. Method 200 may begin with step 201 in which the sequence information of the DNA target is obtained. This sequence information will provide the number of base pairs in the target sequence, i.e., in the amplicon. In step 202, the change in entropy $\Delta S^0$ is calculated. The entropy can be calculated by multiplying the number of base pairs in the target sequence by the entropy per DNA base pair, e.g., $-24.85\ \text{cal mol}^{-1}\text{K}^{-1}$. In step 203, the $T_m$ of the DNA in the reference sample is determined. In step 204, the change in enthalpy $\Delta H^0$ is calculated. The $\Delta H^0$ can be calculated by multiplying the $T_m$ of the DNA in the reference sample by the change in entropy $\Delta S^0$. In step 205, the ratio of the concentration of the DNA in the reference sample to the concentration of the DNA in the sample is determined. In step 206, the $\Delta T_m$ due to the concentration effect is calculated, such as by equation 7 above. In step 207, the $T_m$ of the DNA in the sample is determined. The determinations of the $T_m$ of the DNA in the reference sample in step 203 and of the DNA in the sample in step 207 can be made at the same time. In step 208, the corrected $T_m$ of the DNA in the sample is determined, such as by equation 8 above.

Figure 3:
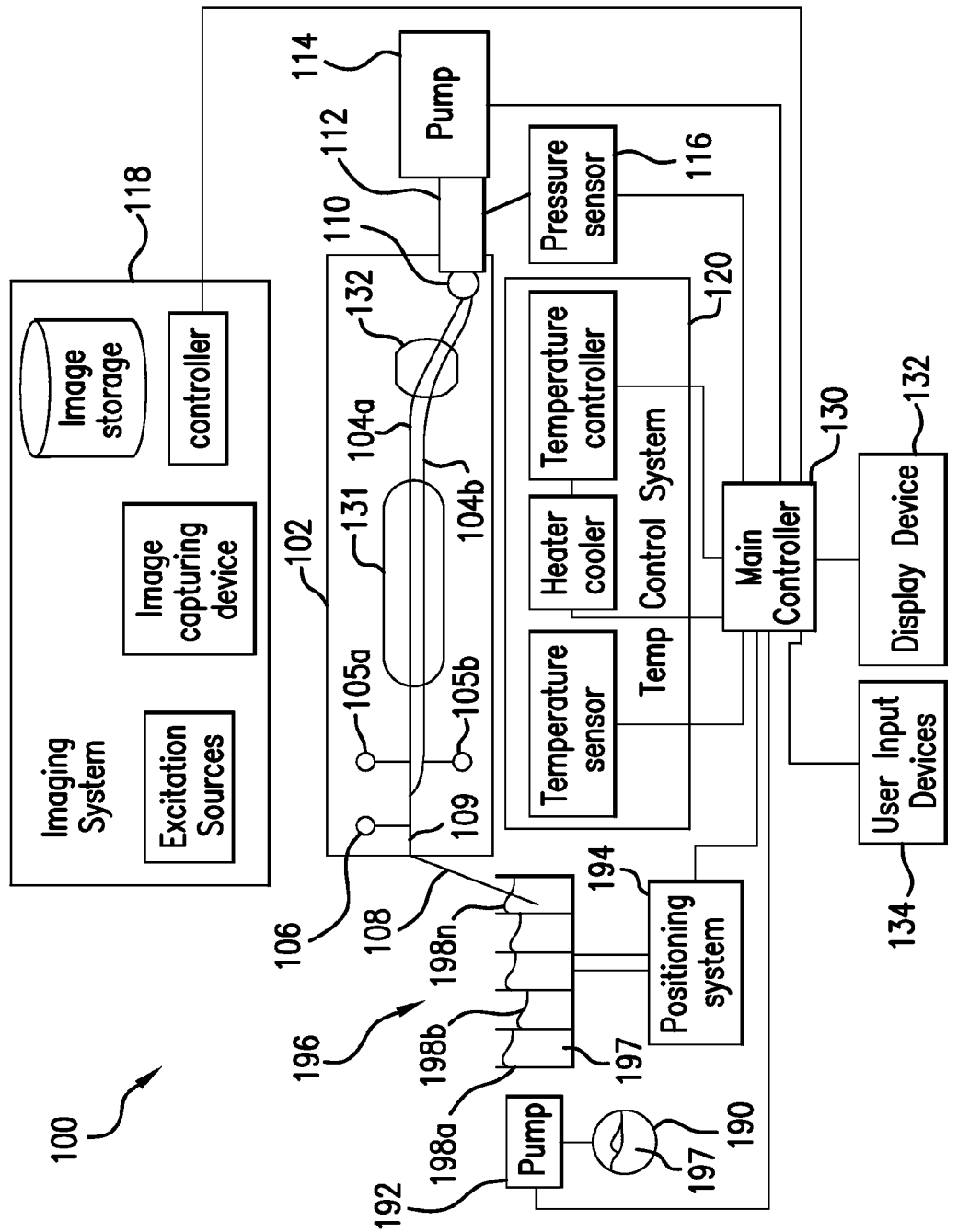
FIG. 3 illustrates a microfluidic device in accordance with some aspects of the present invention.

In accordance with other aspects, the present invention also provides a system for temperature correction in thermal melt analysis due to the effect of the nucleic acid concentration. An example of a suitable system in accordance with some aspects of the invention is illustrated in connection with FIG. 3. As illustrated in FIG. 3, system 100 may include a microfluidic device 102. Microfluidic device 102 may include one or more microfluidic channels 104. In the examples shown, device 102 includes two microfluidic channels, channel 104a and channel 104b. Although only two channels are shown in the exemplary embodiment, it is contemplated that device 102 may have fewer than two or more than two channels. For example, in some embodiments, device 102 includes eight channels 104.

Device 102 may include two DNA processing zones, a DNA amplification zone 131 (e.g., PCR zone 131) and a DNA melting zone 132. A DNA sample traveling through the PCR zone 131 may undergo PCR, and a DNA sample passing through melt zone 132 may undergo high resolution thermal melting. As illustrated in FIG. 3, PCR zone 131 includes a first portion of channels 104 and melt zone 132 includes a second portion of channels 104, which is down stream from the first portion.

Device 102 may also include a sipper 108. Sipper 108 may be in the form of a hollow tube. Sipper 108 has a proximal end that is connected to an inlet 109 which inlet couples the proximal end of sipper 108 to channels 104. Device 102 may also include a common reagent well 106 which is connected to inlet 109. Device 102 may also include a locus specific reagent well 105 for each channel 104. For example, in the embodiment shown, device 102 includes a locus specific reagent well 105a, which is connected to channel 104a, and may include a locus specific reagent well 105b which is connected to channel 104b. Device 102 may also include a waste well 110 for each channel 104.

The solution that is stored in the common reagent well 106 may contain dNTPs, polymerase enzymes, salts, buffers, surface-passivating reagents, one or more non-specific fluorescent DNA detecting molecules, a fluid marker and the like. The solution that is stored in a locus specific reagent well 105 may contain PCR primers, a sequence-specific fluorescent DNA probe or marker, salts, buffers, surface-passivating reagents and the like.

In order to introduce a sample solution into the channels 104, system 100 may include a well plate 196 that includes a plurality of wells 198, at least some of which contain a sample solution (e.g., a solution containing a DNA sample). In the embodiment shown, well plate 196 is connected to a positioning system 194 which is connected to a main controller 130.

Main controller 130 may be implemented, for example, using a PXI-8105 controller which is available from National Instruments Corporation of Austin, Tex. Positioning system 194 may include a positioner (e.g., the MX80 positioner available from Parker Hannifin Corporation of PA ("Parker")) for positioning well plate 196, a stepping drive (e.g., the E-AC Microstepping Drive available from Parker) for driving the positioner, and a controller (e.g., the 6K4 controller available from Parker) for controlling the stepping drive.

To introduce a sample solution into the channels 104, the positioning system 194 is controlled to move well plate 196 such that the distal end of sipper 108 is submerged in the sample solution stored in one of the wells 198. FIG. 3 shows the distal end of 108 being submerged within the sample solution stored in well 198n.

In order to force the sample solution to move up the sipper and into the channels 104, a vacuum manifold 112 and pump 114 may be employed. The vacuum manifold 112 may be operably connected to a portion of device 102 and pump 114 may be operably connected to manifold 112. When pump 114 is activated, pump 114 creates a pressure differential (e.g., pump 114 may draw air out of a waste well 110), and this pressure differential causes the sample solution stored in well 198n to flow up sipper 108 and through inlet channel 109 into channels 104. Additionally, this causes the reagents in wells 106 and 105 to flow into a channel. Accordingly, pump 114 functions to force a sample solution and real-time PCR reagents to flow through channels 104. As illustrated in FIG. 3, melt zone 132 is located downstream from PCR zone 131. Thus, a sample solution will flow first through the PCR zone and then through the melting zone.

Referring back to well plate 196, well plate 196 may include a buffer solution well 198a. In one embodiment, buffer solution well 198a holds a buffer solution 197. Buffer solution 197 may comprise a conventional PCR buffer, such as a conventional real-time (RT) PCR buffer. Conventional PCR buffers are available from a number of suppliers, including: Bio-Rad Laboratories, Inc., Applied Biosystems, Roche Diagnostics, and others.

In order to achieve PCR for a DNA sample flowing through the PCR zone 131, the temperature of the sample must be cycled, as is well known in the art. Accordingly, in some embodiments, system 100 includes a temperature control system 120. The temperature control system 120 may include a temperature sensor, a heater/cooler, and a temperature controller. In some embodiments, a temperature control system 120 is interfaced with main controller 130 so that main controller 130 can control the temperature of the samples flowing through the PCR zone and the melting zone. Main controller 130 may be connected to a display device for displaying a graphical user interface. Main controller 130 may also be connected to user input devices 134, which allow a user to input data and commands into main controller 130.

To monitor the PCR process and the melting process that occur in PCR zone 131 and melt zone 132, respectively, system 100 may include an imaging system 118. Imaging system 118 may include an excitation source, an image capturing device, a controller, and an image storage unit. Other aspects of a suitable system in accordance with some aspects of the invention are disclosed in U.S. patent application Ser. No. 11/770,869, incorporated herein by reference in its entirety.

The system 100 further includes an appropriately controllable computer in communication with the user input devices 134, display device 132 and the main controller 130. The computer receives information from, among many sources, the imaging system 118 and temperature control system 120 and enables the determination of the $T_m$ of a nucleic acid in a sample and thus the identification of the nucleic acid in accordance with some aspects of the invention.

According to this aspect, the system for system for correcting a melting temperature of a nucleic acid in a sample comprises a temperature compensation module capable of determining a temperature compensation value from a ratio of the concentration of the nucleic acid in a reference sample to the concentration of the nucleic acid in the sample and a measured melting temperature of the nucleic acid in the reference sample. In accordance with one embodiment, the temperature compensation module comprises an appropriately programmed computer or software stored on a computer readable medium (e.g., a non-volatile storage device or other storage device), where the software is configured such that when executed by a computer, the software enables the computer to determine a temperature compensation value.

The system further comprises a correction module capable of correcting the measured melting temperature of the nucleic acid in the sample by subtracting the temperature compensation value from the measured melting temperature of the nucleic acid in the sample to provide a corrected melting temperature of the nucleic acid in the sample. In accordance with one embodiment, the correction module comprises an appropriately programmed computer or software stored on a computer readable medium, where the software is configured such that when executed by a computer, the software enables the computer to determine the corrected melting temperature for the nucleic acid in the sample.

In some embodiments, the temperature compensation module determines the change of enthalpy ($\Delta H^0$) of the nucleic acid in the reference sample. In other embodiments, $\Delta H^0$ of the nucleic acid in the reference sample is determined by the equation $T_{m1\ (measured)} \times N_{base\ pair} \times \Delta S_{bp}$, wherein $T_{m1\ (measured)}$ is the measured melting temperature of the nucleic acid in the reference sample, $N_{base\ pair}$ is the number of base pairs in the nucleic acid and $\Delta S_{bp}$ is the change in entropy per base pair. In further embodiments, the temperature compensation value is $\Delta T_m$, wherein $\Delta T_m$ is $T_{m2}-T_{m1}$, in which $T_{m1}$ is the measured melting temperature of the nucleic acid in the reference sample and $T_{m2}$ is the melting temperature resulting from a difference in concentration of the nucleic acid and is determined as described herein.

In one embodiment, the samples further include a fluorescent dye for determining the ratio of concentrations. Suitable fluorescent dyes for detecting denaturation of molecules are well known in the art and include those described herein, such as the double-strand specific dyes of the SYBR Green family of dyes and LCGreen Plus. Any suitable fluorescent dye can be used in the methods of the invention. In a further embodiment, the ratio of concentrations is determined by the ratio of fluorescence intensities.

In one embodiment, the system further comprises a measuring unit capable of measuring the melting temperature of the nucleic acid of the sample and the nucleic acid of the reference sample. In further embodiments, the measuring unit further measures the ratio of the concentration of the nucleic acid in the reference sample to the nucleic acid in the sample.

EXAMPLES

The present invention is described by reference to the following Examples, which are offered by way of illustration and are not intended to limit the invention in any manner. Standard techniques well known in the art or the techniques specifically described below were utilized.

Example 1

Correction of $T_m$ for Known Concentration of Sample DNA

A known concentration of DNA was used for DNA sample C1 which was used as the reference. A second DNA sample C2 was prepared by diluting DNA sample C1. The DNA concentration ratio of C1 to C2 was 5. The samples were subjected to polymerase chain reaction amplification with the size of the amplicon being 70 bp. Following the amplification, the $T_m$ was measured for both the C1 reference sample and the C2 sample. The measured $T_m$ for C1 was 78.66° C. (i.e., $T_{m1\ (measured)}$) and the measured $T_m$ for C2 was 77.82° C. (i.e., $T_{m2\ (measured)}$). The difference in $T_m$ was caused by concentration change in the sample DNA. The corrected melting temperature $T_{m2\ (corrected)}$ for C2 is calculated in accordance with the following steps.

First, the change in enthalpy, $\Delta H^0$, is calculated. $\Delta H^0$ can be calculated using several equations. In one embodiment, $\Delta H^0$ can be calculated using the equation $$\Delta H^0 = T_{m\ (measured)} \times \Delta S^0,$$

where $\Delta S^0$ is the change in entropy and $T_{m\ (measured)}$ is the measured melting temperature in degrees K. $\Delta S^0$ can be calculated using several equations. In one embodiment, $\Delta S^0$ can be calculated by the equation $$\Delta S^0 = N_{base\ pair} \times \Delta S_{bp},$$

where N is the number of base pairs in the amplicon and $\Delta S_{bp}$ is the change in entropy per DNA base pair. The change in entropy per DNA base pair, $\Delta S^{bp}$, is roughly $-24.85$ cal mol$^{-1}$K$^{-1}$ (Owczarzy et al., *Biopolymers* 44:217-239 (1997)). Using these equations, $\Delta H^0$ is calculated according to the equation $$T_{m1\ (measured)} \times N_{base\ pair} \times \Delta S^{bp},$$

Using this equation, $\Delta H^0$ is calculated as $-6.1197 \times 10^5$ cal/mol (i.e., (273.15° K.+78.66° K.)×70×(−24.85 cal mol$^{-1}$K$^{-1}$)). This $\Delta H^0$ value is converted to J/mol by dividing the value (i.e., $-6.1197 \times 10^5$ cal/mol) by $2.3901 \times 10^{-1}$ cal/J to yield $-2.5604 \times 10^6$ J/mol.

Second, the change in the melting temperature, $\Delta T_m$, resulting from the difference in concentration is calculated. $\Delta T_m$ is equal to $T_{m2}-T_{m1}$. For the reference sample, C1, $T_{m1}$ is $T_{m1\ (measured)}$. $T_{m2}$ is calculated according to the following equation $$\frac{1}{T_{m2}} = \frac{1}{T_{m1}} - \frac{R\ln\left(\frac{C1}{C2}\right)}{\Delta H^0},$$

where R is the gas constant (8.314472 J/Kmol). Using this equation, $T_{m2}$ is calculated as follows:

$$\frac{1}{T_{m2}} = \frac{1}{351.81} - \frac{8.314482\ln(5)}{-2.5604 \times 10^6}$$

$$= \frac{1}{351.81} + \frac{8.314482 \times (1.6)}{2.5604 \times 10^6}$$

$$\frac{1}{T_{m2}} = 2.8424434 \times 10^{-3} + 5.1957 \times 10^{-6}$$

$$= 2.8476391 \times 10^{-3}$$

$$T_{m2} = 351.17$$

$\Delta T_m$ is equal to $T_{m2}-T_{m1}$=351.17−351.81=−0.64° K.

Third, the corrected melting temperature of C2 is calculated. $T_{m2\ (corrected)}$ is calculated according to the following equation $$T_{m2\ (corrected)} = T_{m2\ (measured)} - \Delta T_m.$$

Using this equation, $T_{m2\ (corrected)}$ is calculated as 78.46° C. (i.e., (273.15+77.82)−(−0.64)−273.15). Thus, after correction of $T_m$ for C2, the $T_m$ for C1 is 78.66° C. and the $T_m$ for C2 is 78.46° C.

Example 2

Correction of $T_m$ for Unknown Concentration of Sample DNA

Polymerase chain reaction amplifications were performed for the sickle cell trait (Sickle) and for Coagulation Factor V (CFV) in samples of human genomic DNA. A reference sample (C1) for Sickle was prepared by adding about 1000 copies of the Sickle target sequence for producing the Sickle amplicon to a solution. The size of the Sickle amplicon was 118 base pairs. Similarly, a reference sample (C1) for CFV was prepared by adding about 1000 copies of the CFV target sequence, i.e., amplicon, to a solution. The size of the CFV amplicon was 158 base pairs. A DNA dye was added to the reference samples and to the samples of human genomic DNA (C2 for Sickle and C2 for CFV). The measured fluorescence intensity (FI) is proportional to the DNA concentration. The FI was measured for all samples after completion of the polymerase chain reaction amplifications and before measuring the melting temperatures. The FI ratio was determined, and this ratio is the ration of the concentrations of C1 to C2. The FIs and FI ratio for the amplifications performed in this example are shown in the following table.

| PCR product | FI of C1 | FI of C2 | Ratio of FI (C1/C2) | N (amplicon length) |
|---|---|---|---|---|
| Sickle | 18 | 0.9 | 20 | 118 |
| CFV | 21 | 1.0 | 21 | 158 |

The melting temperature ($T_m$) for each of the amplification products was measured. The measured melting temperatures are shown in the following table.

|  | C1 | C2 |
|---|---|---|
| $T_{m\ (measured)}$, Sickle | 80.96 | 79.63 |
| $T_{m\ (measured)}$, CFV | 80.76 | 78.86 |

The reference samples, C1, are used to calculate the corrected $T_m$ of the genomic samples (C2) as shown in Example 1. Thus, the change in enthalpy ($\Delta H^0$) was calculated for both Sickle and CFV according to the equation $T_{m1\ (measured)} \times N_{base\ pair} \times \Delta S_{bp}$. The calculated values for $\Delta H^0$ for Sickle and CFV are shown in the following table.

|  | $T_{m1\ (measured)}$ (° K) | N (amplicon length) | $\Delta H^0$ (J/mol) |
|---|---|---|---|
| Sickle | 354.11 | 118 | $-4.3444 \times 10^6$ |
| CFV | 353.91 | 158 | $-5.8138 \times 10^6$ |

The change in melting temperature ($\Delta T_m$) was then calculated for each of the Sickle sample and the CFV sample using the following equation as shown in Example 1.

$$\frac{1}{T_{m2}} = \frac{1}{T_{m1}} - \frac{R\ln\left(\frac{C1}{C2}\right)}{\Delta H^0}$$

The calculated values for $T_{m2}$ and $\Delta T_m$ for Sickle and CFV are shown in the following table.

| | C1/C2 | ΔH (J/mol) | $T_{m1}$ (° K) | $T_{m2}$ (° K) | $\Delta T_m = T_{m2} - T_{m1}$ |
|---|---|---|---|---|---|
| Sickle | 20 | $-4.3444 \times 10^6$ | 354.11 | 353.39 | $-0.72$ |
| CFV | 21 | $-5.8138 \times 10^6$ | 353.91 | 353.36 | $-0.55$ |

The corrected $T_m$ ($T_{m\ (measured)} - \Delta T_m$) for the genomic samples (C2) for the Sickle and the CFV assays were calculated and the values are shown in the following table.

| PCR product | $T_{m\ (measured)}$ C1 | $T_{m\ (corrected)}$ C2 |
|---|---|---|
| Sickle | 80.96 | 80.35 |
| CFV | 80.76 | 79.41 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A computerized method for correcting a measured melting temperature of a nucleic acid in a sample, wherein the melting temperature refers to the dissociation of double stranded DNA into single stranded DNA, wherein a first reference sample comprising a nucleic acid, and a second nucleic acid containing sample are utilized, comprising:
    a) determining a ratio of the concentration of the nucleic acid in the first reference sample to the concentration of the nucleic acid in the second nucleic acid containing sample, wherein the first and second samples contain identical nucleic acids in different concentrations;
    b) using an imaging system and a temperature control system in communication with a computer to measure the melting temperature of the nucleic acid in the second nucleic acid containing sample ($T_{m\ second\ sample\ measured}$) and the melting temperature of the nucleic acid in the first reference sample ($T_{m1}$);
    c) determining a temperature compensation value from said ratio and determining the change of enthalpy ($\Delta H^0$) of the nucleic acid in the first reference sample, wherein the temperature compensation value is $\Delta T_m$, wherein $\Delta T_m$ is $T_{m2} - T_{m1}$, wherein $T_{m1}$ is the measured melting temperature of the nucleic acid in the first reference sample and $T_{m2}$ is calculated by the equation $$\frac{1}{T_{m2}} = \frac{1}{T_{m1}} - \frac{R \ln\left(\frac{C1}{C2}\right)}{\Delta H^0},$$

wherein R is the gas constant and C1/C2 is the ratio of the concentration of the nucleic acid in the first reference sample to the concentration of the nucleic acid in the second nucleic acid containing sample; wherein the determining a temperature compensation value is performed by the computer; and
    d) correcting the measured melting temperature of the nucleic acid in the second nucleic acid containing sample with the temperature compensation, wherein the correcting the measured melting temperature is performed by the computer based upon the formula $T_{m\ second\ sample\ corrected} = T_{m\ second\ sample\ measured} - \Delta T_m$.

2. The method of claim 1, wherein $\Delta H^0$ of the nucleic acid in the first reference sample is determined by the equation $T_{m1\ (measured)} \times N_{base\ pair} \times \Delta S_{bp}$, wherein $T_{m1\ (measured)}$ is the measured melting temperature of the nucleic acid in the first reference sample, $N_{base\ pair}$ is the number of base pairs in the nucleic acid and $\Delta S_{bp}$ is the change in entropy per base pair.

3. The method of claim 2, wherein the measured melting temperature of the nucleic acid in the second nucleic acid containing sample is corrected by subtracting $\Delta T_m$ from the measured melting temperature of nucleic acid in the second nucleic acid containing sample.

4. The method of claim 1, wherein the measured melting temperature of the nucleic acid in the second nucleic acid containing sample is corrected by subtracting $\Delta T_m$ from the measured melting temperature of nucleic acid in the second nucleic acid containing sample.

5. The method of claim 1, wherein the ratio is determined after amplification of the nucleic acid in the second nucleic acid containing sample and amplification of the nucleic acid in the first reference sample.

6. The method of claim 5, wherein the ratio is determined by measuring fluorescence of the nucleic acid in the second nucleic acid containing sample and of the nucleic acid in the first reference sample.

7. The method of claim 5, wherein the amplifications are performed in microchannels.

8. The method of claim 7, wherein the amplifications are performed in continuous flow in the microchannels.

9. The method of claim 8, wherein the melting temperatures are measured in a continuous melt.

10. A system for correcting a melting temperature of a nucleic acid in a sample, wherein the melting temperature refers to the dissociation of double stranded DNA into single stranded DNA, comprising:
(a) a first reference sample and a second sample, the first and second samples containing identical nucleic acids in different concentrations;
(b) an imaging system and a temperature control system in communication with the first reference sample and the second sample to measure data associated with the nucleic acid melting process;
(c) a computer system in communication with the imaging system and the temperature control system, the computer system to determine the melting temperature of the nucleic acid in the first reference sample ($T_{m1}$) and a melting temperature of the nucleic acid in the second sample ($T_{m\ second\ sample\ measured}$) based upon the data associated with the nucleic acid melting process;
wherein the computer system determines a temperature compensation value from a ratio of the concentration of the nucleic acid in a first reference sample to the concentration of the nucleic acid in the second nucleic acid containing sample and the determined melting temperature of the nucleic acid in the first reference sample and a change of enthalpy ($\Delta H^0$) of the nucleic acid in the reference sample,
wherein the temperature compensation value is $\Delta T_m$, wherein $\Delta T_m$ is $T_{m2}-T_{m1}$,
wherein $T_{m1}$ is the measured melting temperature of the nucleic acid in the first reference sample and $T_{m2}$ is the melting temperature resulting from a difference in concentration of the nucleic acid,
wherein $T_{m2}$ is calculated by the equation $$\frac{1}{T_{m2}} = \frac{1}{T_{m1}} - \frac{R\ln\left(\frac{C1}{C2}\right)}{\Delta H^0},$$

wherein R is the gas constant and C1/C2 is the ratio of the concentration of the nucleic acid in the first reference sample to the concentration of the nucleic acid in the second nucleic acid containing sample; and
wherein the computer system subtracts the temperature compensation value from the measured melting temperature of the nucleic acid in the second nucleic acid containing sample to provide a corrected melting temperature of the nucleic acid in the second nucleic acid containing sample based upon the formula $T_{m\ second\ sample\ corrected} = T_{m\ second\ sample\ measured} - \Delta T_m$.

11. The system of claim 10, wherein $\Delta H^0$ of the nucleic acid in the first reference sample is determined by the equation $T_{m1\ (measured)} \times N_{base\ pair} \times \Delta S_{bp}$, wherein $T_{m1\ (measured)}$ is the measured melting temperature of the nucleic acid in the first reference sample, $N_{base\ pair}$ is the number of base pairs in the nucleic acid and $\Delta S_{bp}$ is the change in entropy per base pair.

12. The system of claim 10, wherein the computer system includes memory containing instructions for determining the temperature compensation value.

* * * * *